(12) United States Patent
De Visser

(10) Patent No.: US 10,226,015 B2
(45) Date of Patent: Mar. 12, 2019

(54) *PERONOSPORA* RESISTANCE IN *SPINACIA* SP

(71) Applicant: POP VRIEND RESEARCH B.V., Andijk (NL)

(72) Inventor: Jan De Visser, Andijk (NL)

(73) Assignee: POP VRIEND RESEARCH B.V., Andijk (NL)

( * ) Notice: Subject to any disclaimer, the term of this patent is extended or adjusted under 35 U.S.C. 154(b) by 221 days.

(21) Appl. No.: 14/937,714

(22) Filed: Nov. 10, 2015

(65) Prior Publication Data

US 2017/0127642 A1   May 11, 2017

(51) Int. Cl.
    *A01H 5/12*    (2018.01)
    *A01H 6/02*    (2018.01)
    *A01H 1/04*    (2006.01)

(52) U.S. Cl.
    CPC ............... *A01H 5/12* (2013.01); *A01H 1/04* (2013.01); *A01H 6/028* (2018.05)

(58) Field of Classification Search
    None
    See application file for complete search history.

(56) References Cited

U.S. PATENT DOCUMENTS

| | | | |
|---|---|---|---|
| 9,295,220 B2 * | 3/2016 | Jansen ............... | C12N 15/8241 |
| 9,402,363 B1 | 8/2016 | Feitsma et al. | |
| 9,615,531 B2 | 4/2017 | Den Braber | |
| 9,615,532 B2 | 4/2017 | Den Braber | |
| 9,624,507 B2 | 4/2017 | Dijkstra | |
| 9,848,574 B2 | 12/2017 | Baerends | |
| 2009/0300786 A1 * | 12/2009 | Baerends ............... | A01H 5/12 800/268 |
| 2012/0107458 A1 | 5/2012 | den Braber | |
| 2012/0222147 A1 | 8/2012 | Dijkstra | |
| 2013/0055422 A1 | 2/2013 | Baerends | |
| 2013/0055454 A1 | 2/2013 | den Braber | |
| 2013/0055455 A1 | 2/2013 | den Braber | |
| 2013/0055456 A1 | 2/2013 | den Braber | |
| 2013/0198882 A1 | 8/2013 | Baerends | |
| 2013/0198884 A1 | 8/2013 | Dijkstra | |
| 2013/0205420 A1 | 8/2013 | Baerends | |
| 2013/0230635 A1 * | 9/2013 | Den Braber ............. | A01H 1/04 426/615 |
| 2015/0020231 A1 | 1/2015 | Baerends | |
| 2015/0082483 A1 * | 3/2015 | Dijkstra ............... | A01H 1/04 800/279 |
| 2015/0101073 A1 | 4/2015 | Brugmans et al. | |
| 2015/0240256 A1 | 8/2015 | Brugmans et al. | |
| 2017/0027127 A1 * | 2/2017 | Dijkstra ............... | A01H 5/12 |
| 2017/0142924 A1 * | 5/2017 | Feitsma ............... | A01H 5/12 |
| 2017/0327839 A1 * | 11/2017 | Feitsma ............. | C12N 15/8282 |

FOREIGN PATENT DOCUMENTS

| | | |
|---|---|---|
| AU | 2014221305 A1 | 4/2015 |
| EP | 2848114 A1 | 3/2015 |
| NZ | 630628 A | 4/2015 |
| WO | WO 2015/036378 A1 | 3/2015 |
| WO | WO 2015/036469 A1 * | 3/2015 |
| WO | WO 2015/054339 A1 | 4/2015 |
| WO | WO 2017/084724 A1 * | 5/2017 |

OTHER PUBLICATIONS

Feng et al., Plant Des 98:145-52 (2014).*
Brenner, Int'l Spinach Conference, 14 (2009).*
Koike & Correll, Salinas Valley Ag (2014).*
Correll & Koike, CLGRB Annual Report (2014).*
Correll et al., Eur J Plant Pathol 129:193-205 (2011).*
Irish et al., Plant Dis 91:1392-96 (2007).*
Hallavant & Ruas, Veget Hist Archaeobot 23(2):153-65 (2014).*
Correll et al., Eur J Plant Pathol 129:193-205, 195 (2011).*
Merriam-Webster, "representative" https://www.merriam-webster.com/dictionary (accessed Dec. 29, 2017).*
U.S. Appl. No. 14/937,696, filed Nov. 10, 2015, Pop Vriend Research B.V.
Feng, C. et al., 2014, Identification of New Races and Deviating Strains of the Spinach Downy Mildew Pathogen *Peronospora farinosa* f. sp. *spinaciae*, Plant Disease 98:1, 145-152.
Wisley trials, 1991, Spinach, Autumn sown.
Nunhems Vegetable Seeds (USA and Canada); Crops; Spinach Fresh Market; retrieved from the internet on Feb. 8, 2017 at http://nunhemsusa.com/www/NunhemsInternet.nsf/id/US_EN_Spinach_Fresh_Mark et.
Rijk Zwann, "Products & Services", Dromedary RZ F1, http://www.rijkzwaanusa.com/wps/wcm/connect/RZ+USA/Rijk+Zwaan/Products_and_Services/Products/Crops/Spinach?pcpage=3&frm=1&varname=DROMEDARY%20RZ%20F1%20(51-330)&his=c293LCwwO2hhenYsLDA7cGxhbnQsLDA7cmFkaW9zY2hlZCxoYXJ2LDA7, May 2016.
Rijk Zwann, "Products & Services", Antelope RZ F1, http://www.rijkzwaanusa.com/wps/wcm/connect/RZ+USA/Rijk+Zwaan/Products_and_Services/Products/Crops/Spinach?pcpage=3&frm=1&varname=ANTELOPE%20RZ%20F1%20(51-324)&his=c293LCwwO2hhenYsLDA7cGxhbnQsLDA7cmFkaW9zY2hlZCxoYXJ2LDA 7, May 20, 2016.
Rijk Zwann, "Products & Services", Gazelle RZ F1, http://www.rijkzwaanusa.com/wps/wcm/connect/RZ+USA/Rijk+Zwaan/Products_and_Services/Products/Crops/Spinach?pcpage=3&frm=1&varname=GAZELLE%20RZ%20F1%20(51-326)&his=c293LCwwO2hhenYsLDA7cGxhbnQsLDA7cmFkaW9zY2hlZCxoYXJ2LDA7, May 2016.
Variety Description Pigeon, Feb. 25, 2011, 3 pages.
Rijk Zwann, "Products & Services", Pigeon RZ F1, http://www.rijkzwaanusa.com/wps/wcm/connect/RZ+USA/Rijk+Zwaan/Products_and_Services/Products/Crops/Spinach?pcpage=3&frm=1&varname=PIGEON%20RZ%20F1%20(51-313)&his=c293LCwwO2hhenYsLDA7cGxhbnQsLDA7cmFkaW9zY2hlZCxoYXJ2LDA7, May 2016.
Plantum Press release, "Denomination of Pfs:15, a new race of downy mildew in spinach", Sep. 2, 2014, 2 pages.

(Continued)

Primary Examiner — Russell T Boggs
(74) Attorney, Agent, or Firm — Morrison & Foerster LLP

(57) ABSTRACT

The current invention concerns a spinach plant comprising resistance against *Peronospora farinosa* races 1-9, 11-15 and isolate UA1014APLP.

10 Claims, No Drawings

(56) References Cited

OTHER PUBLICATIONS

PCT/EP2016/077322, Pop Vriend Research B.V., Search Report and Written Opinion.
Correll, J. et al, Project Title: Race diversity and the biology of the spinach downy mildew pathogen, CLGRB Annual Report, Apr. 1, 2013 to Mar. 31, 2014.
Correll, J. et al, Spinach: better management of downy mildew and white rust through genomics, European Journal of Plant Pathology, 2011, 129:193-205.
Irish et al. (2008). "Characterization of a resistance locus (Pfs-1) to the spinach downy mildew pathogen (*Peronospora farinosa f.* sp. *spinaciae*) and development of a molecular marker linked to Pfs-1," Phytopathology, 98:894-900.

\* cited by examiner

PERONOSPORA RESISTANCE IN SPINACIA SP

TECHNICAL FIELD

The invention pertains to the technical field of to a spinach plant comprising a gene or locus which leads to a broad spectrum resistance to *Peronospora farinosa* f. sp. *spinaciae* (Pfs). The invention also relates to progeny of said spinach plant, to propagation material of said spinach plant, to a cell of said spinach plant, to seed of said spinach plant, and to harvested leaves of said spinach plant. This invention further relates to use of a spinach plant in breeding to confer resistance against *Peronospora farinosa* f. sp. *spinaciae*.

BACKGROUND

Spinach (*Spinacia oleracea*) is a flowering plant from the Amaranthaceae family that is grown as a vegetable. The consumable parts of spinach are the leaves from the vegetative stage. Spinach is sold loose, bunched, in prepacked bags, canned, or frozen. There are three basic types of spinach, namely the savoy, semi-savoy and smooth types. Savoy has crinkly and curly leaves. Flat or smooth leaf spinach has in general broad, smooth leaves. Semi-savoy is a variety with slightly crinkled leaves. The main market for spinach is baby-leaf. Baby spinach leaves are usually of the flat-leaf variety and usually the harvested leaves are not longer than about eight centimeter. These tender, sweet leaves are sold loose rather than in bunch. They are often used in salads, but can also be lightly cooked. Downy mildew—in spinach caused by the pathogen *Peronospora farinosa* f. sp. *spinaciae* (formerly known as *P. effusa*)—is a major threat for spinach growers, because it affects the harvested plant parts, namely the leaves. Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f. sp. *spinaciae* is 9 to 12° C., and it is facilitated by a high relative humidity. When pathogens are deposited on a humid leaf surface they can readily germinate and infect the leaf. Pathogen growth is optimal between 8 and 20° C. and a relative humidity of ≥80%, and within 6 and 13 days after infection growth can be observed. Pathogens of *P. farinosa* can survive in the soil for up to 3 years, or in seeds or living plants. In recent years various resistance genes have been identified that provide spinach plants with a resistance against downy mildew. However, it has been observed that previously resistant spinach cultivars can again become susceptible to the pathogen. Investigations revealed that the cultivars themselves had not changed, and that the loss of downy mildew resistance must therefore be due to *P. farinosa* overcoming the resistance in these spinach cultivars. The downy mildew races that were able to infect resistant spinach cultivars have been determined on a differential reference set, used to test spinach cultivars for resistance. The differential set comprises a series of spinach cultivars (hybrids) that have different resistance patterns to the currently identified pathogenic races. To date 15 pathogenic races of spinach downy mildew (Pfs) have been officially identified and characterized. Races 4 through 10 have been identified between 1990 and 2009, which illustrates the versatility and adaptability of the pathogen to overcome resistances in spinach. In 2014, isolate UA1014APLP (also known as UA1014) was identified by the Correll lab of Arkansas.

In different geographical regions different combinations of pathogenic races or isolates occur, and the spinach industry therefore has a strong demand for spinach cultivars that are resistant to as many relevant downy mildew races as possible, preferably to all races that may occur in their region, and even to the newest threats that cannot be countered with the resistances that are present in the commercially available spinach cultivars.

It is crucial to stay at the forefront of developments in this field, as *Peronospora* continuously develops the ability to break the resistances that are present in commercial spinach varieties.

For this reason new resistance genes are very valuable assets, and they form an important research focus in spinach breeding. The goal of spinach breeders is to rapidly develop spinach varieties with a resistance to as many *Peronospora* races as possible, including the latest identified. To date, 15 Pfs races are officially recognized and made publicly available from the Department of Plant Pathology, University of Arkansas, Fayetteville, Ark. 72701, USA, and also from NAK Tuinbouw, Sotaweg 22, 2371 GD Roelofarendsveen, the Netherlands. Pfs 15 was officially recognized in 2014 by the International Working Group on *Peronospora farinosa* (IWGP). Recently identified isolate UA1014APLP is yet to be officially recognized as a race, but is to date already of importance to breeders.

It is the object of the invention to provide a spinach plant, conferring resistance to various *Peronospora* races and/or isolates, including the ones that have been most recently identified.

SUMMARY OF THE INVENTION

The present invention provides therefore a spinach plant according to claim 1. The spinach plant comprises resistance against *Peronospora farinosa* races 1-9, 11-15, and isolate UA1014APLP. More in particular, said plant is obtainable by introgression from a plant grown from seeds of which a representative sample has been deposited with NCIMB under NCIMB accession number 42393. The plant provides a broad spectrum of *Peronospora farinosa* resistance which is stably transferred to the progeny.

Definitions

The indefinite article "a" or "an" does not exclude the possibility that more than one of the element is present, unless the context clearly requires that there be one and only one of the elements. The indefinite article "a" or "an" thus usually means "at least one".

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one or two loci or genes (or phenotypic characteristics due to these specific loci or genes), but which can otherwise differ from one another enormously as regards the other loci or genes.

"Spinach" or "cultivated spinach" or "cultivated *Spinacia oleracea*" refers herein to plants of the species *Spinacia oleracea* (or seeds from which the plants can be grown), and parts of such plants, bred by humans for food and having good agronomic characteristics. This includes any cultivated spinach, such as breeding lines (e.g. backcross lines, inbred lines), cultivars and varieties (open pollinated or hybrids). This includes any type of spinach, such as savoy, flat- or smooth-leaf spinach or semi-savoy types. Wild spinach (i.e. not cultivated spinach) or wild relatives of spinach, such as *Spinacia tetrandra* and *Spinacia turkestanica*, are not encompassed by this definition.

As used herein, the term "plant" includes the seed (from which the plant can be grown), the whole plant or any parts such as plant organs (e.g., harvested or non-harvested leaves, etc.), plant cells, plant protoplasts, plant cell- or tissue cultures from which whole plants can be regenerated, propagating or non-propagating plant cells, plants cells which are not in tissue culture (but which are for example in vivo in a plant or plant part), plant callus, plant cell clumps, plant transplants, seedlings, plant cells that are intact in plants, plant clones or micro-propagations, or parts of plants (e.g., harvested tissues or organs), such as plant cuttings, vegetative propagations, embryos, pollen, ovules, flowers, leaves, heads, seeds (produced on the plant after self-fertilization or cross-fertilization), clonally propagated plants, roots, stems, stalks, root tips, grafts, parts of any of these and the like, or derivatives thereof, preferably having the same genetic make-up (or very similar genetic make-up) as the plant from which it is obtained. Also any developmental stage is included, such as seedlings, cuttings prior or after rooting, mature and/or immature plants or mature and/or immature leaves. When "seeds of a plant" are referred to, these either refer to seeds from which the plant can be grown or to seeds produced on the plant, after self-fertilization or cross-fertilization.

"Somatic cells" and "reproductive cells" can be distinguished, whereby somatic cells are cells other than gametes (e.g. ovules and pollen), germ cells and gametocytes. Gametes, germ cells and gametocytes are "reproductive cells."

"Tissue Culture" or "cell culture" refers to an in vitro composition comprising isolated cells of the same or a different type or a collection of such cells organized into plant tissue. Tissue cultures and cell cultures of spinach, and regeneration of spinach plants therefrom, is well known and widely published (see, e.g. Nguyen et al., 2013, Plant Biotechnology Reports, Vol. 7 Issue 1, p 99).

"Harvested plant material" refers herein to plant parts (e.g., leaves detached from the whole plant) which have been collected for further storage and/or further use.

"Harvested seeds" refers to seeds harvested from a line or variety, e.g., produced after self-fertilization or cross-fertilization and collected.

"Harvested leaves" as used herein refers to spinach leaves, i.e., the plant without the root system, for example substantially all (harvested) leaves.

Progeny" or "progenies" or "descendants" as used herein refers to offspring, or the first and all further descendants derived from (obtainable from) (derivable from or obtained from) a plant of the invention that comprises (retains) the resistance gene in homozygous or heterozygous form and/or the resistance phenotype described herein. Progeny may be derived by regeneration of cell culture or tissue culture, or parts of a plant, or selfing of a plant, or by producing seeds of a plant. In further embodiments, progeny may also encompass spinach plants derived from crossing of at least one spinach plant with another spinach plant of the same or another variety or (breeding) line, and/or backcrossing, and/or inserting of a locus into a plant and/or mutation. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Also double haploid plants are progeny.

"Plant line" is for example a breeding line which can be used to develop one or more varieties.

"F1, F2, F3, etc." refers to the consecutive related generations following a cross between two parent plants or parent lines. The plants grown from the seeds produced by crossing two plants or lines is called the F1 generation. Selfing the F1 plants results in the F2 generation, etc.

Hybrid" refers to the seeds harvested from crossing one plant line or variety with another plant line or variety, and the plants or plant parts grown from said seeds.

"F1 hybrid" plant (or F1 hybrid seed) is the generation obtained from crossing two non-isogenic inbred parent lines. Thus, F1 hybrid seeds are seeds from which F1 hybrid plants grow.

An "interspecific hybrid" refers to a hybrid produced from crossing a plant of one species, e.g. *S. oleracea*, with a plant of another species, e.g. *S. tetrandra* or *S. turkestanica*.

"Crossing" refers to the mating of two parent plants. Equally "Cross-pollination" refers to fertilization by the union of two gametes from different plants.

"Selfing" refers to the self-pollination of a plant, i.e. to the union of gametes from the same plant.

"Backcrossing" refers to a breeding method by which a (single) trait, such as Pfs resistance conferred by a resistance gene, can be transferred from one genetic background (also referred to as "donor"; generally but not necessarily this is an inferior genetic background) into another genetic background (also referred to as "recurrent parent"; generally but not necessarily this is a superior genetic background). An offspring of a cross (e.g. an F1 plant obtained by crossing a wild spinach or wild relative of spinach with a cultivated spinach; or an F2 plant or F3 plant, etc., obtained from selfing the F1) is "backcrossed" to the parent with the superior genetic background, e.g. to the cultivated parent.

After repeated backcrossing, the trait of the donor genetic background, e.g. the resistance gene, will have been incorporated into the recurrent genetic background. The terms "gene converted" or "conversion plant" or "single locus conversion" in this context refer to plants which are developed by backcrossing wherein essentially all of the desired morphological and/or physiological characteristics of the recurrent parent are recovered in addition to the one or more genes (e.g. the resistance gene) transferred from the donor parent.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, the—resistance gene can be obtained, identified, selected, and/or transferred.

"Regeneration" refers to the development of a plant from in vitro cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting off) leaf, pollen, embryo, cotyledon, hypocotyl, cells, protoplasts, meristematic cell, root, root tip, pistil, anther, flower, shoot tip, shoot, stem, fruit, and petiole. When a whole plant is regenerated by vegetative propagation, it is also referred to as a "vegetative propagation" or a "vegetatively propagated plant".

"Single locus converted (conversion) plant" refers to plants which are developed by plant breeding techniques comprising or consisting of backcrossing, wherein essentially all of the desired morphological and/or physiological characteristics of a spinach plant are recovered in addition to the characteristics of the single locus having been transferred into the plant via the backcrossing technique and/or by genetic transformation.

"Transgene" or "chimeric gene" refers to a genetic locus comprising a DNA sequence which has been introduced into the genome of a spinach plant by transformation. A plant comprising a transgene stably integrated into its genome is referred to as "transgenic plant".

"Transgene" or "chimeric gene" refers to a genetic locus comprising a DNA sequence which has been introduced into the genome of a spinach plant by transformation. A plant comprising a transgene stably integrated into its genome is referred to as "transgenic plant".

"Pfs" or "*Peronospora farinosa*" or "downy mildew" refers to races of the pathogen *Peronospora farinosa* fsp. *spinaciae*. Pfs1-15 refer to the officially recognized races, which can be differentiated on the differential hosts of spinach and which can be obtained from the Naktuinbouw, P.O. Box 40, 2370 AA Roelofarendsveen, The Netherlands, or via references provided by the ISF (International Seed Federation).

"Differential hosts" or "differentials" refers to the differential hosts of spinach for distinguishing Pfs races 1-15, which can be obtained from the Naktuinbouw, P.O. Box 40, 2370 AA Roelofarendsveen, The Netherlands, or via references provided by the ISF (International Seed Federation).

A "Pfs resistant plant" or "downy mildew resistant plant" or a plant having "Pfs resistance" or a "Pfs resistant phenotype" refers to a spinach plant which is resistant against one or more pathogenic races and/or pathogenic isolates of Pfs, as determined in a qualitative resistance assay under controlled environmental conditions. In such a resistance assay a plurality of plants (e.g. at least 2 replicates of at least 10 plants) of a genotype, are inoculated with a sporangia suspension of the race or isolate and incubated under suitable conditions. After a suitable incubation period (e.g. 7, 8, 9, 10, 11 or more days after inoculation) the plants are evaluated for symptoms. Susceptible controls should show sporulation at the time of symptom evaluation. Any plant showing sporulation on the cotyledons (and/or on the true leaf/leaves) is considered "susceptible", while any plant not showing any sporulation on the cotyledons (and/or on the true leaf/leaves) is considered "resistant". A plant genotype with more than 85% of the inoculated plants (preferably more than 95%) being classified as "resistant" plants is considered to be resistant against the race or isolate. In the test >85% of inoculated plants (preferably more than 95% of plants) of the susceptible control plant, such as cultivar Viroflay, should show sporulation. Suitable tests are described in Irish et al. 2007 (Plant Disease Vol91 No. 11, in Materials and Methods on page 1392-1394), or in Correll et al. 2010, "Guidelines for Spinach Downy Mildew: *Peronspora ferinosaf* sp. *spinaciae* (Pfs)" found on the website of the ISF (International Seed Federation).

The term "locus" (loci plural) means a specific place or places or a site on a chromosome where for example a gene or genetic marker is found.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "gene" means a (genomic) DNA sequence comprising a region (transcribed region), which is transcribed into a messenger RNA molecule (mRNA) in a cell, and an operably linked to regulatory region (e.g. a promoter). Different alleles of a gene are thus different alternative forms of the gene, which may be in the form of e.g. differences in one or more nucleotides of the genomic DNA sequence (e.g. in the promoter sequence, the exon sequences, intron sequences, etc.), mRNA and/or amino acid sequence of the encoded protein.

"Allelism test" refers to a genetic test whereby it can be tested whether a phenotype, such as Pfs resistance, seen in two plants, is determined by the same gene or by different genes. For example, the plants to be tested are crossed with each other, the F1 is selfed and the segregation of the phenotypes amongst the F2 progeny is determined. Other segregating populations can equally be made (e.g. backcross populations). The ratio of segregation of the phenotype indicates if the genes are allelic (alleles of the same gene) or non-allelic (different, independent genes).

"Introgression fragment" or "introgression segment" or "introgression region" refers to a chromosome fragment (or chromosome part or region) which has been introduced into another plant of the same or related species by crossing or traditional breeding techniques, such as backcrossing, i.e. the introgressed fragment is the result of breeding methods referred to by the verb "to introgress" (such as backcrossing). In spinach, wild spinach or wild relatives of spinach are often used to introgress fragments of the wild genome into the genome of cultivated spinach. Such a spinach plant thus has a "genome of *Spinacia oleracea*", but comprises in the genome a fragment of a wild spinach or spinach relative. It is understood that the term "introgression fragment" never includes a whole chromosome, but only a part of a chromosome. The introgression fragment can be large, e.g. even half of a chromosome, but is preferably smaller, such as about 15 Mb or less, such as about 10 Mb or less, about 9 Mb or less, about 8 Mb or less, about 7 Mb or less, about 6 Mb or less, about 5 Mb or less, about 4 Mb or less, about 3 Mb or less, about 2 Mb or less, about 1 Mb (equals 1,000,000 base pairs) or less, or about 0.5 Mb (equals 500,000 base pairs) or less, such as about 200,000 bp (equals 200 kilo base pairs) or less, about 100,000 bp (100 kb) or less, about 50,000 bp (50 kb) or less, about 25,000 bp (25 kb) or less.

"Physical distance" between loci (e.g. between molecular markers and/or between phenotypic markers) on the same chromosome is the actual physical distance expressed in base pairs (bp), kilo base pairs (kb) or megabase pairs (Mb).

"Genetic distance" between loci (e.g. between molecular markers and/or between phenotypic markers) on the same chromosome is measured by frequency of crossing-over, or recombination frequency (RF) and is indicated in centimorgans (cM). One cM corresponds to a recombination frequency of 1%. If no recombinants can be found, the RF is zero and the loci are either extremely close together physically or they are identical. The further apart two loci are, the higher the RF.

A genetic element, a locus, an introgression fragment or a gene or allele conferring a trait (such as resistance against Pfs) is said to be "obtainable from" or can be "obtained from" or "derivable from" or can be "derived from" or "as present in" or "as found in" a plant or seed if it can be transferred from the plant or seed in which it is present into another plant or seed in which it is not present (such as a line or variety) using traditional breeding techniques without resulting in a phenotypic change of the recipient plant apart from the addition of the trait conferred by the genetic element, locus, introgression fragment, gene or allele. The terms are used interchangeably and the genetic element, locus, introgression fragment, gene or allele can thus be transferred into any other genetic background lacking the trait. Not only seeds deposited and comprising the genetic element, locus, introgression fragment, gene or allele can be used, but also progeny/descendants from such seeds which have been selected to retain the genetic element, locus, introgression fragment, gene or allele, can be used and are encompassed herein, such as commercial varieties developed from the deposited seeds or from descendants thereof. Whether a plant comprises the same genetic element, locus, introgression fragment, gene or allele as obtainable from the deposited seeds can be determined by the skilled person using one or more techniques known in the art, such as phenotypic assays, whole genome sequencing, molecular marker analysis, trait mapping, chromosome painting, allelism tests and the like.

The term "traditional breeding techniques" encompasses herein crossing, backcrossing, selfing, selection, chromosome doubling, double haploid production, embryo rescue, the use of bridge species, protoplast fusion, marker assisted selection, mutation breeding etc. as known to the breeder (i.e. methods other than genetic modification/transformation/transgenic methods), by which, for example, the resistance according to the current invention can be obtained, identified, selected, and/or transferred.

DETAILED DESCRIPTION OF THE INVENTION

The present invention concerns a spinach plant comprising resistance against *Peronospora farinosa* races 1-9, 11-15 and isolate UA1014APLP, more specifically races Pfs1, Pfs2, Pfs3, Pfs4, Pfs5, Pfs6, Pfs7, Pfs8, Pfs9, Pfs11, Pfs12, Pfs13, Pfs14 and Pfs15, and isolate UA1014APLP. The resistance is a broad range resistance.

More specifically the plant is obtainable by (or obtained by, or derivable from, or derived from) introgression from a plant grown from seeds of which a representative sample has been deposited with NCIMB under NCIMB accession number 42393 or any plant derived therefrom.

The resistance trait may be inherited by a single gene, preferably a dominant gene.

In another embodiment, said resistance is conferred by two or more genes, or a multilocus.

In fact, the resistance locus or loci (and the Pfs resistance phenotype conferred thereby), can be transferred from the seeds deposited under NCIMB 42393, or from progeny of said seeds, into any spinach line or variety by traditional breeding techniques and can confer race 1-9, 11-15 and isolate UA1014APLP resistance (and optionally resistance against new pathogenic isolates) onto another spinach plant. Thus, for example, a spinach plant of the invention can be used as male or female parent in a cross with another spinach plant, and progeny, such as F1, F2, F3, or further generations of selfing and/or backcross progeny (e.g. BC1, BC2, BC1S1, BC2S1, BC1S2, etc.) can be identified and selected, whereby the progeny comprise the same Pfs resistance phenotype as the initial plant of the invention. Selection of progeny for the presence of the resistance can, therefore, be carried out using a disease resistance assay as described herein, whereby resistance against one or more (or all) of the Pfs races is tested in the progeny.

Whether a spinach plant genotype (i.e. a spinach line or variety) comprises resistance against one or more Pfs races or isolates can be tested using qualitative disease resistance assays under controlled environment conditions. Different protocols of such assays exist and can be used by the person skilled in the art. In short, seedlings of a plurality of plants of the plant genotype to be tested (e.g. at least 6, 7, 8, 9, 10, 11, 12, 13, 14, 15, 16, 17, 18, 19, 20, or more) are inoculated with inoculum of the Pfs race and the seedlings are incubated under conditions which are favorable to the pathogen. Several days after incubation, the plants are assessed for infection symptoms, especially sporulation on the cotyledons and/or leaves (e.g. first true leaf), and each plant is categorized as "resistant" (showing no signs of sporulation) or "susceptible" (showing sporulation). If a certain percentage of all plants of a genotype are classified as "resistant", e.g. more than about 85%, 90%, 95%, 98%, 99% (or even 100%), then the spinach plant genotype is resistant to the race tested. Obviously, also one or more control plants (e.g. a susceptible line or variety, a resistant line or variety) should be included in the assay using the same treatment(s) and environmental conditions, to ensure that the assay works as expected.

Alternatively or in addition to the phenotypic assay, selection or identification of a spinach plant (e.g. a progeny plant) comprising the resistance gene or locus/loci of the invention may be achieved by detecting one or more molecular markers linked to the resistance gene or locus. This aspect will be described elsewhere herein.

In one of the embodiments of the invention, the spinach plant is an inbred line, especially an inbred line which can be used as a parent for F1 hybrid seed production. In another embodiment of the invention, the spinach plant is a hybrid, especially an F1 hybrid. An F1 hybrid may be generated by crossing a first inbred parent line which comprises the resistance gene or locus/loci, preferably in homozygous form, with a second inbred parent line. The first inbred parent line may be a line developed from using seeds deposited under NCIMB 42393 or from progeny of plants grown from these seeds, whereby the progeny retain the Pfs resistance phenotype (and the resistance gene or locus/loci).

The second inbred parent line may be any spinach line, i.e. it may completely lack Pfs resistance, or it may comprise a different Pfs resistance gene (and different resistance phenotype) or it may also comprise the resistance gene or locus/loci according to the current invention.

As mentioned, the spinach plant according to the invention may be any type of spinach. For example, the spinach plant may be a savoy type, a semi-savoy type or flat- or smooth leaved spinach.

In other words, the resistance can be introduced into any other spinach plant by introgression from a plant grown from seeds of which a representative sample was deposited under NCIMB 42393, or any spinach plant derived therefrom and comprising the gene or locus/loci. The deposited seeds are therefore a source of the resistance of the invention, as are spinach plants not directly obtained from the deposit, but for example indirectly obtained (e.g. later released commercial varieties) and which contain the resistance gene or locus/loci of the invention.

The resistance of the current invention was identified in wild material from a genebank and was introduced through backcrossing into *S. oleracea*. In one aspect, therefore, a spinach plant is provided comprising resistance against at least Pfs 1-9, 11-15 and isolate UA1014APLP and possibly new pathogenic isolates, wherein said resistance against *Peronospora farinosa* is conferred by an introgression fragment from wild spinach or from a wild relative of spinach.

In one embodiment, the introgression fragment is the fragment as found in (and as obtainable from; or obtained from; or derivable from; or derived from) spinach seeds, a representative sample of seeds having been deposited under accession number NCIMB 42393. The fragment can be identified by various methods, such as chromosome painting or sequencing the spinach genome and identifying chromosome parts which are introgressions from wild spinach or wild relatives of spinach. The fragment can also be identified by one or more molecular markers (e.g. SNP markers, AFLP markers, RFLP markers, etc.), especially molecular markers which are polymorphic between cultivated spinach and the wild introgression fragment.

In another embodiment, the introgression fragment is derived from the fragment as found in spinach seeds, a representative sample of seeds having been deposited under accession number NCIMB 42393, whereby the introgression fragment is shorter but retains the resistance gene or locus/loci (and the Pfs resistance phenotype conferred by the gene). Spinach plants comprising such shorter introgression fragments can be generated by crossing a plant of the invention with another spinach plant and selecting recombinant progeny which retain the resistance phenotype conferred by the resistance gene or locus/loci, but which contain a shorter introgression fragment.

In one aspect a method is provided for generating spinach plant comprising resistance against at least Pfs races 1-9, 11-15 and isolate UA1014APLP, comprising the steps of:

a) Providing a spinach plant comprising resistance against at least Pfs races 1-9, 11-15 and isolate UA1014APLP, b) Crossing said spinach plant with another spinach plant to produce F1 seeds;

c) Optionally selfing the plants grown from F1 seeds one or more times to produce F2, F3 or further generation selfing progeny;

d) Identifying (or selecting) spinach plants grown from F1, F2, F3 or further generation selfing progeny which have resistance against at least Pfs races 1-9, 11-15 and isolate UA1014APLP;

e) Optionally crossing said identified (or selected) F1 progeny or selfing progeny to the spinach plant of step b), to produce a backcross progeny;

f) Optionally selecting backcross progeny comprising resistance against at least Pfs races 1-9, 11-15 and isolate UA1014APLP.

In another embodiment a method for generating a spinach plant comprising resistance against at least *Peronospora farinosa* races 1-9, 11-15 and isolate UA1014APLP is provided comprises the steps of:

a) Providing a spinach plant comprising an introgression fragment obtainable from (or as in) accession NCIMB 42393, which introgression fragment confers resistance against at least *Peronospora farinosa* races 1-9, 11-15 and isolate UA1014APLP;

b) Crossing said spinach plant with another spinach plant, for example with a spinach plant which is susceptible against one or more of *Peronospora farinosa* races 1-9, 11-15 and isolate UA1014APLP, to produce F1 seeds;

c) Optionally selfing the plants grown from F1 seeds one or more times to produce F2, F3 or further generation selfing progeny;

d) Identifying spinach plants grown from F1, F2, F3 or further generation selfing progeny which have resistance against at least *Peronospora farinosa* races 1-9, 11-15 and isolate UA1014APLP and/or which comprise the introgression fragment or a resistance-conferring part of the introgression fragment;

e) Optionally crossing said identified F1 progeny or selfing progeny to the spinach plant of step b), to produce a backcross progeny;

f) Optionally selecting backcross progeny which comprises resistance against at least *Peronospora farinosa* races 1-9, 11-15 and isolate UA1014APLP and/or which comprise the introgression fragment or a resistance-conferring part of the introgression fragment.

Regarding both methods, the following is encompassed herein.

In one aspect the plant of a) comprises the resistance trait as found in seeds deposited under accession number NCIMB 42393. The spinach plant may be the plant grown from the seeds of the deposit or any spinach plant made using, or having used, the seed deposit and which retains the Pfs resistance phenotype (and the gene or locus/loci conferring it). This includes commercial spinach varieties which were made using the seed deposit. Thus, the spinach plant of a) comprises the resistance gene/locus/loci according to the invention, e.g. as found in (or as obtainable from; obtained from; derivable from; derived from) NCIMB 42393. The plant in a) may therefore be a plant grown from seeds, a representative sample of which has been deposited under NCIMB 42393.

Selections (or identification) in step d) and/or f) may be made based on the phenotype (i.e. using a Pfs resistance assay) and/or based on molecular methods, such as detection of molecular markers linked to the resistance gene or locus/loci, or other methods such as sequencing.

In step b) the spinach plant is, in one aspect, crossed with a spinach plant which is susceptible against at least one of the Pfs races against which the plant of a) is resistant. If the second parent in b) is a spinach plant which is susceptible against at least one of the Pfs races against which the plant of a) is resistant, then the selection in step (d) and/or (f) may be based on selecting plants which now have resistance against that race.

Steps e) and f) may be repeated one or more times.

In the above methods also plants can be selected and/or identified which retain the Pfs resistance phenotype according to the current invention, but which have a smaller introgression fragment. This can have advantages, as negative traits coupled to the wild introgression fragment can thereby be removed. Initial introgression fragments from wild sources can be quite large, e.g. 20 Mb or 30 Mb. It is therefore preferred to reduce the size of the introgression fragment by recombination and to select plants comprising smaller introgression fragments, but which retain the resistance-conferring part. So, spinach with all sizes of introgression fragments originating from (or derived from; or derivable from; or obtained from; or obtainable from) seeds deposited under accession number NCIMB 42393 are included herein, as long as the Pfs resistance conferring part is retained in the spinach plant. As mentioned, the presence can be tested and selected phenotypically and/or using molecular methods known in the art.

Also plants obtainable or obtained by any of the above methods are embodiments of the invention.

The plants according to the invention may be any cultivated spinach, e.g. savoy, semi-savoy, flat- or smooth leaved spinach. They may be inbred lines, F1 hybrids, double haploids, transgenic plants, mutant plants, etc.

Plants of the invention can be used to generate progeny, which have or retain the Pfs resistance phenotype as obtainable from (as present in; as derivable from; as obtained or derived from) seeds deposited under NCIMB 42393. To generate progeny, a spinach according to the invention can be selfed and/or crossed one or more times with another spinach plant and seeds can be collected. The presence of resistance according to the current invention or the gene/locus/loci responsible therefor in the progeny plants can be determined by the Pfs resistance phenotype and/or molecular methods, such as molecular markers (e.g. SNP markers) closely linked to the gene or locus/loci.

Also seeds from which the plants of the invention can be grown are provided.

In one embodiment, the use of a spinach plant, of which representative seeds have been deposited under accession number NCIMB 42393, or progeny thereof (e.g. obtained by selfing), for generating a spinach plant comprising Pfs resistance against at least *Peronospora farinosa* races 1-9, 11-15 and isolate UA1014APLP is provided.

In another embodiment, the use of a spinach plant comprising resistance against at least *Peronospora farinosa* races 1-9, 11-15 and isolate UA1014APLP conferred by an introgression fragment obtainable from (or as present in; as derivable from; as obtained or derived from) seeds deposited under accession number NCIMB 42393, or from progeny thereof (e.g. obtained by selfing), for generating spinach plant comprising resistance against at least *Peronospora farinosa* 1-9, 11-15 and isolate UA1014APLP is provided.

It is noted that also allelism tests can be used to determine whether the resistance gene in a spinach plant is the same gene/locus/loci or a different gene/locus/loci as the resistance gene/locus/loci as present in NCIMB 42393 (or in progeny thereof). So, NCIMB 42393 (or progeny) can be crossed with another spinach plant comprising the same resistance phenotype and in progeny of such a cross one can determine in which ratios the phenotype segregates. So in one aspect a spinach plant is provided comprising resistance against *P. farinosa* races 1-9, 11-15 and isolate UA1014APLP, wherein said resistance gene/locus/loci conferring said resistance phenotype is the gene/locus/loci as present in NCIMB 42393 (or progeny thereof), as determinable in an allelism test. Allelism tests for dominant genes are known in the art and are e.g. described in Hibberd et al. 1987 (Phytopathology 77: 1304-1307).

Also seeds from which any of the plants of the invention can be grown are provided, as are containers or packages containing or comprising such seeds. Seeds can be distinguished from other seeds due to the presence of the resistance gene/locus/loci, either phenotypically (based on plants having the resistance phenotype according to the current invention) and/or using molecular methods.

In one aspect, seeds are packaged into small and/or large containers (e.g., bags, cartons, cans, etc.). The seeds may be pelleted prior to packing (to form pills or pellets) and/or treated with various compounds, such as seed coatings.

Pelleting creates round or rounded shapes, which are easily sown with modern sowing machines. A pelleting mixture typically contains seeds and at least glue and filler material. The latter could be, for example, clay, mica, chalk or cellulose. In addition, certain additives can be included to improve particular properties of the pellet, e.g., a seed treatment formulation comprising at least one insecticidal, acaricidal, nematicidal or fungicidal compound can be added directly into the pelleting mixture or in separate layers. A seed treatment formulation can include one of these types of compounds only, a mixture of two or more of the same type of compounds or a mixture of one or more of the same type of compounds with at least one other insecticide, acaricide, nematicide or fungicide.

Formulations especially suitable for the application as a seed treatment can be added to the seed in the form of a film coating including also the possibility of using the coating in or on a pellet, as well as including the seed treatment formulation directly into the pellet mixture. Characteristically, a film coating is a uniform, dust-free, water permeable film, evenly covering the surface of all individual seeds.

Besides the formulation, the coating mixture generally also contains other ingredients such as water, glue (typically a polymer), filler materials, pigments and certain additives to improve particular properties of the coating. Several coatings can be combined on a single seed.

In addition, several combinations with film coating are possible: the film coating can be added on the outside of the pellet, in between two layers of pelleting material, and directly on the seed before the pelleting material is added. Also more than 1 film coating layer can be incorporated in a single pellet. A special type of pelleting is encrusting. This technique uses less filler material, and the result is a 'mini-pellet'.

Seeds may also be primed. Spinach is often primed. Priming is a water-based process that is performed on seeds to increase uniformity of germination and emergence from the soil, and thus enhance vegetable stand establishment. Priming decreases the time span between the emergence of the first and the last seedlings. Methods how to prime spinach seeds are well known in the art.

In a further aspect plant parts, obtained from (obtainable from) a plant of the invention are provided herein, and containers or packages comprising said plant parts.

In a preferred embodiment the plant parts are leaves of spinach plants of the invention, preferably harvested leaves, or parts of these. Leaves may be loose, bunched, fresh (e.g. in bags), frozen, blanched or boiled. Leaves may be fresh or processed, they may be part of food or feed products, such as salads, etc.

Other plant parts, of plants of the invention, include stems, cuttings, petioles, cotyledons, flowers, anthers, pollen, ovaries, roots, root tips, protoplasts, callus, microspores, stalks, ovules, shoots, seeds, embryos, embryo sacs, cells, meristems, buds etc.

Seeds include for example seeds produced on the plant of the invention after selfpollination or seed produced after cross-pollination, e.g. pollination of a plant of the invention with pollen from another spinach plant or pollination of another spinach plant with pollen of a plant of the invention.

In a further aspect, the plant part is a plant cell. In still a further aspect, the plant part is a non-regenerable cell or a regenerable cell. In another aspect the plant cell is a somatic cell.

A non-regenerable cell is a cell which cannot be regenerated into a whole plant through in vitro culture, but the non-regenerable cell may be in a plant or plant part (e.g. leaves) of the invention.

In a further aspect the plant cell is a reproductive cell, such as an ovule or pollen. These cells are haploid. When they are regenerated into whole plants, they comprise the haploid genome of the starting plant. If chromosome doubling occurs (e.g. through chemical treatment), a double haploid plant can be regenerated. In one aspect the plant of the invention, comprising the resistance gene/locus/loci is a haploid or a double haploid spinach plant.

Moreover, there is provided an in vitro cell culture or tissue culture of spinach plants of the invention in which the cell- or tissue culture is derived from a plant parts described above, such as, for example and without limitation, leaves, pollen, embryos, cotyledon, hypocotyls, callus, meristematic cells, roots, root tips, anthers, flowers, seeds or stems, somatic cells, reproductive cells.

Also provided are spinach plants regenerated from the above-described plant parts, or regenerated from the above-described cell or tissue cultures, said regenerated plant having a Pfs resistance phenotype, i.e. retains the resistance gene/locus/loci (or the introgression fragment comprising the resistance gene/locus/loci) of the invention. These plants can also be referred to as vegetative propagations of plants of the invention.

Also provided are harvested leaves of plants of the invention and packages comprising a plurality of leaves of plants of the invention. These leaves thus comprise the resistance of the invention, detectable by e.g. linked molecular markers or phenotypically (for the originally used whole plant and/or regenerated plant).

The invention also provides for a food or feed product comprising or consisting of a plant part described herein. The food or feed product may be fresh or processed, e.g., canned, steamed, boiled, fried, blanched and/or frozen etc. Examples are salad or salad mixtures comprising leaves or parts of leaves of plants of the invention.

A spinach plant of the invention or a progeny thereof retaining the Pfs resistance phenotype conferred by the gene/locus/loci and/or retaining the introgression fragment comprising the gene/locus/loci, as present in NCIMB 42393, and parts of the afore-mentioned plants, can be suitably packed for, e.g., transport, and/or sold fresh. Such parts encompass any cells, tissues and organs obtainable from the seedlings or plants, such as but not limited to: leaves, cuttings, pollen, parts of leaves, and the like.

Leaves may be harvested immature, as baby-leaf or baby spinach, or mature. A plant, plants or parts thereof may be packed in a container (e.g., bags, cartons, cans, etc.) alone or together with other plants or materials. Parts can be stored and/or processed further. Encompassed are therefore also food or feed products comprising one or more of such parts, such leaves or parts thereof obtainable from a plant of the invention, a progeny thereof and parts of the afore-mentioned plants. For example, containers such as cans, boxes, crates, bags, cartons, Modified Atmosphere Packaging, films (e.g. biodegradable films), etc. comprising plant parts of plants (fresh and/or processed) of the invention are also provided herein.

In another embodiment, plants and parts of spinach plants of the invention, and progeny of spinach plants of the invention are provided, e.g., grown from seeds, produced by sexual or vegetative reproduction, regenerated from the above-described plant parts, or regenerated from cell or tissue culture, in which the reproduced (seed propagated or vegetatively propagated) plant comprises resistance against at least Pfs races 1-9, 11-15 and isolate UA1014APLP.

As mentioned before, whether or not a plant, progeny or vegetative propagation comprises the Pfs resistance phenotype as conferred by the current invention can be tested phenotypically using e.g. the Pfs disease resistance assays as described above; and/or using molecular techniques such as molecular marker analysis, DNA sequencing (e.g. whole genome sequencing to identify the wild introgression), chromosome painting, etc.

In one embodiment, the resistance gene/locu/loci obtainable from (obtained from; as found in) plants deposited under NCIMB 42393, or progeny thereof, can be combined with other *Peronospora farinosa* resistance genes or resistance loci or with other traits, such resistance against bacteria (e.g. *Pseudomonas syringae* pv. *spinacea; Erwinia carotovora*), fungi (e.g. *Albugo occidentalis; Colletotrichum dematium* f sp. *spinaciae; Stemphylium botryosum* f sp. *spinaciae*), viruses (e.g. viruses causing curly top disease) or nematodes. This can be done by traditional breeding techniques, e.g. by backcrossing in order to introduce one or more traits into a plant of the invention or in order to introduce the gene/locus/loci of a plant of the invention into another spinach plant comprising such one or more additional traits. Thus, in one aspect a plant of the invention is used as a donor of the resistance according to the current invention, while in another aspect a plant of the invention is used as recipient of one or more other traits.

Furthermore, the invention provides for progeny comprising or retaining the Pfs resistance phenotype, such as progeny obtained by, e.g., selfing one or more times and/or cross-pollinating a plant of the invention with another spinach plant of a different variety or breeding line, or with a spinach plant of the invention one or more times. In particular, the invention provides for progeny that retain the resistance gene/locus/loci (conferring the Pfs resistance phenotype) of (as found in) NCIMB 42393. In one aspect the invention provides for a progeny plant comprising the resistance according to the current invention, such as a progeny plant that is produced from a spinach plant comprising the resistance according to the current invention by one or more methods selected from the group consisting of: selfing, crossing, mutation, double haploid production or transformation.

Mutation may be spontaneous mutations or human induced mutations or somaclonal mutations. In one embodiment, plants or seeds of the invention may also be mutated (by e.g. irradiation, chemical mutagenesis, heat treatment, TILLING, etc.) and/or mutated seeds or plants may be selected (e.g. natural variants, somaclonal variants, etc.) in order to change one or more characteristics of the plants.

Similarly, plants of the invention may be transformed and regenerated, whereby one or more chimeric genes are introduced into the plants.

Transformation can be carried out using standard methods, such as Agrobacterium tumefaciens mediated transformation or biolistics, followed by selection of the transformed cells and regeneration into plants.

A desired trait (e.g. genes conferring pest or disease resistance, herbicide, fungicide or insecticide tolerance, etc.) can be introduced into the plants, or progeny thereof, by transforming a plant of the invention or progeny thereof with a transgene that confers the desired trait, wherein the transformed plant retains the resistance according to the current invention and the Pfs resistance phenotype conferred by it and contains the desired trait.

The resistance gene or locus/loci may be transferred to progeny by further breeding. In one aspect progeny are F1 progeny obtained by crossing a plant of the invention with another plant or S1 progeny obtained by selfing a plant of the invention. Also encompassed are F2 progeny obtained by selfing the F1 plants, or further generation progeny. "Further breeding" encompasses traditional breeding techniques (e.g. selfing, crossing, backcrossing), marker assisted breeding, and/or mutation breeding. In one embodiment, the progeny have the Pfs resistance phenotype of NCIMB 42393.

In one aspect haploid plants and/or double haploid plants of plant of the invention are encompassed herein, which comprise resistance against at least *Peronospora farinosa* races 1-9, 11-15 and isolate UA1014APLP, as conferred by the gene/locus/loci or by the introgression fragment comprising the resistance gene. Haploid and double haploid (DH) plants can for example be produced by anther or microspore culture and regeneration into a whole plant. For DH production chromosome doubling may be induced using known methods, such as colchicine treatment or the like. So, in one aspect a spinach plant is provided, comprising Pfs resistance phenotype as described, wherein the plant is a double haploid plant.

In another embodiment the invention relates to a method for producing spinach seed, comprising crossing a plant of the invention with itself or a different spinach plant and harvesting the resulting seed. In a further embodiment the invention relates to seed produced according to this method and/or a spinach plant produced by growing such seed. Thus, a plant of the invention may be used as male and/or female parent, in the production of spinach seeds, whereby the plants grown from said seeds comprise at least *Peronospora farinosa* resistance against races 1-9, 11-15 and isolate UA1014APLP.

Thus, in one aspect progeny of a spinach plant of the invention are provided, wherein the progeny plant is produced by selfing, crossing, mutation, double haploid production or transformation and wherein the progeny retain the resistance gene/locus/loci (and phenotype conferred by it) described herein, i.e. obtainable by crossing a spinach plant, grown from seeds deposited under accession number NCIMB 42393, with another spinach plant. In other words, the resistance gene or locus (or introgression fragment comprising the gene or locus) as present in/found in/as derived from (or as derivable from) seed deposit NCIMB 42393 is retained in the progeny plants.

Molecular markers may also be used to aid in the identification of the plants (or plant parts or nucleic acids obtained therefrom) containing the resistance gene or locus or allele(s). For example, one can develop one or more suitable molecular markers which are closely genetically (and preferably also physically) linked to the resistance gene, locus or allele. This can be done by crossing a resistant spinach plant with a susceptible spinach plant and developing a segregating population (e.g. F2 or backcross population) from that cross. The segregating population can then be phenotyped for Pfs resistance and genotyped using e.g. molecular markers such as SNPs (Single Nucleotide Polymorphisms), AFLPs (Amplified Fragment Length Polymorphisms; see, e.g. EP 534 858), or others, and by software analysis molecular markers which co-segregate with the Pfs resistance trait in the segregating population can be identified and their order and genetic distance (centimorgan distance, cM) to the resistance gene or locus can be identified.

Molecular markers which are closely linked to resistance locus or loci, e.g. markers at a 5 cM distance or less, can then be used in detecting and/or selecting plants (e.g. plants of the invention or progeny of a plant of the invention) or plant parts comprising or retaining the introgression fragment comprising the resistance gene or locus. Such closely linked molecular markers can replace phenotypic selection (or be used in addition to phenotypic selection) in breeding programs, i.e. in Marker Assisted Selection (MAS). Preferably flanking markers are used in MAS, i.e. one marker on either side of the resistance gene or locus/loci.

Any other type of molecular marker and/or other assay that is able to identify the relative presence or absence of a trait of interest in a plant or plant part can also be useful for breeding purposes.

Deposit Information

A total of 2500 seeds of spinach line 'B11-505-3-17' were deposited by Pop Vriend Seeds on 7 Apr. 2015, according to the Budapest Treaty in the National Collection of Industrial, Food and Marine Bacteria Ltd (NCIMB Ltd), Ferguson Building, Craibstone Estate, Bucksburn, Aberdeen AB21 9YA, United Kingdom. The deposit has been assigned NCIMB number 42393. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed. The deposit will be maintained in the NCIMB depository, which is a public depository, for a period of 30 years, or 5 years after the most recent request for a sample of the deposit, or for the enforceable life of the patent, whichever is longer, and will be replaced if a deposit becomes nonviable during that period. Applicant does not waive any rights granted under this patent on this application or under the Plant Variety Protection Act (7 USC 2321 et seq.).

EXAMPLES

Origin of Breeding

Spinach, a sample of seeds of which were deposited as NCIMB 42393, was developed by first crossing a plant of variety Viroflay (*S. oleracea*) with a plant of *S. turkestanica* with accession number KK28. The final outcome was a spinach plant with resistance against races 1-9, 11-15 and isolate UA1014APLP. Observation during the variety selections confirmed that NCIMB 42393 is uniform and stable.

The crossing scheme was as follows:

Step 1: cross between cultivar Viroflay (*S. oleracea*) and *S. turkestanica* accession nr. KK28;

Step 2: crossing of F1 progeny plants from step 1 with cultivar Crocodile (*S. oleracea*);

Step 3: selfing of the plants obtained from step 2 (after selection for Downy mildew resistance); and Step 4: selfing of the plants obtained from step 3 (after selection for Downy mildew resistance).

Seeds resulting from step 4 were grown and Downy mildew test results showed resistance against races 1-9, 11-15 and isolate UA1014APLP.

In accordance with the invention, novel varieties may be created by crossing NCIMB 42393 followed by multiple generations of breeding according to well-known methods. New varieties may be created by crossing with any second plant. Once initial crosses have been made, inbreeding and selection take place to produce new varieties. For development of a uniform line, often five or more generations of selfing and selection are involved. It is supposed that the present invention is not restricted to any form of realization described previously and that some modifications can be added to the presented example of fabrication without reappraisal of the appended claims.

The invention claimed is:

1. A spinach seed, a sample of the seed having been deposited under NCIMB Accession Number 42393.

2. A spinach plant produced by growing the seed of claim 1, wherein the spinach plant is resistant to *Peronospora farinosa* f. sp. *spinaciae* races Pfs:1, Pfs:2, Pfs:3, Pfs:4, Pfs:5, Pfs:6, Pfs:9, Pfs:11, Pfs:12, Pfs:13, Pfs:14, Pfs:15, and isolate UA1014APLP.

3. A plant part from the plant of claim 2.

4. The plant part of claim 3, wherein said part is a stem, a cutting, a flower, a root, a shoot, a leaf, or a portion thereof.

5. The plant part of claim 3, wherein said part is a leaf.

6. The plant part of claim 3, wherein said part is a stem.

7. A pollen grain or an ovule of the plant of claim 2.

8. A method of producing spinach seed, said method comprising crossing the plant of claim 2 with another spinach plant and harvesting seed therefrom.

9. A food product comprising harvested leaves of the spinach plant of claim 2.

10. A container comprising the spinach plant of claim 2 in a growth substrate for harvest of leaves from said spinach plant.

* * * * *